United States Patent
Murakami

(10) Patent No.: US 6,940,537 B2
(45) Date of Patent: Sep. 6, 2005

(54) INSPECTING APPARATUS OF PRINTED STATE OR THE LIKE IN FLEXIBLE PRINTED CIRCUIT BOARD

(75) Inventor: Takehiko Murakami, Fuchu (JP)

(73) Assignee: Minami Co., Ltd., Tokyo (JP)

( * ) Notice: Subject to any disclaimer, the term of this patent is extended or adjusted under 35 U.S.C. 154(b) by 401 days.

(21) Appl. No.: 10/229,810

(22) Filed: Aug. 28, 2002

(65) Prior Publication Data

US 2003/0052968 A1 Mar. 20, 2003

(30) Foreign Application Priority Data

Sep. 17, 2001 (JP) ........................................ 2001-281134

(51) Int. Cl.[7] .................................................. H04B 1/66
(52) U.S. Cl. ........................... 348/126; 348/92; 348/87; 348/94; 702/150; 702/113
(58) Field of Search ............................ 348/126, 92, 87, 348/94, 133; 702/150, 113

(56) References Cited

U.S. PATENT DOCUMENTS 4,858,820 A * 8/1989 Kent ........................... 228/264
5,574,668 A * 11/1996 Beaty ........................... 702/150
5,657,075 A * 8/1997 Roessner ..................... 348/126

* cited by examiner

Primary Examiner—Shawn S. An
(74) Attorney, Agent, or Firm—R. Neil Sudol; Henry D. Coleman; William J. Sapone

(57) ABSTRACT

To provide an inspecting apparatus of a printed state or the like in a flexible printed circuit board which requires no skill, generates no error by oversight and further improves an operation efficiency, a substrate feeding out unit (2), a substrate inverting unit (4), a camera inspecting unit (5), a substrate inverting unit (9) and a defect point marking unit (10) for a printed state or the like are sequentially placed on working tables (1, 1) along a moving direction of a flexible printed circuit board, in this order, the substrate inverting units (4, 9) respectively invert the flexible printed circuit board, the camera inspecting unit (5) detects a print defect point by means of a camera (8), and the defect point marking unit (10) applies a marking to the print defect point by a laser marker (13) on the basis of a signal output from the camera inspecting unit (5).

1 Claim, 2 Drawing Sheets

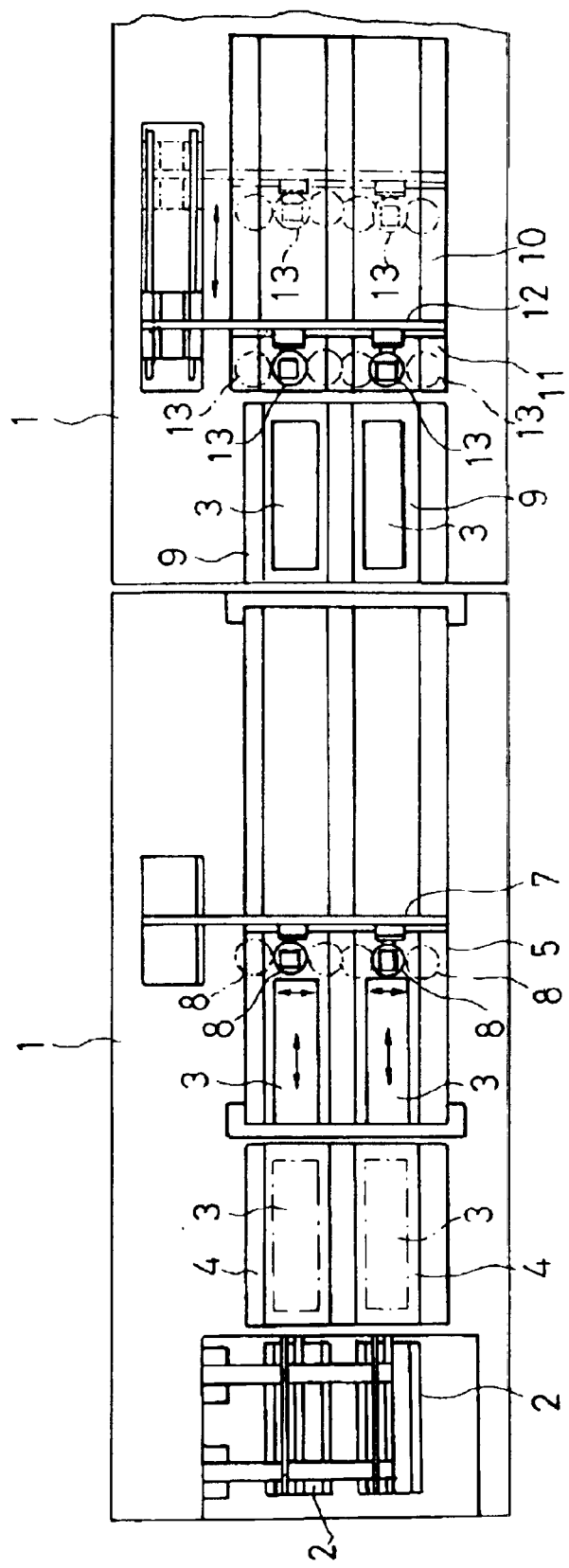

INSPECTING APPARATUS OF PRINTED STATE OR THE LIKE IN FLEXIBLE PRINTED CIRCUIT BOARD

BACKGROUND OF THE INVENTION

1. Field of the Invention

The present invention relates to an inspecting apparatus of a printed state or the like in a flexible printed circuit board.

2. Conventional Art

An inspection of a printed state of a pattern or the like in a flexible printed circuit board has been conventionally performed by a visual inspection. However, in the case of the visual inspection, a considerable skill has been required and an error by oversight has frequently occurred. Further, an operation efficiency is low and a great influence is applied to an operation efficiency of a whole of a continuous operation comprising a printing operation, a parts mounting operation and a reflow operation. Further, in particular, in the case of applying the printing on both of two faces of a flexible printed circuit board, this adverse effect becomes further increased.

SUMMARY OF THE INVENTION

The present invention is made by taking the points mentioned above into consideration, and an object of the present invention is to provide an inspecting apparatus which can solve the problems in the case of the conventional visual inspection by employing a mechanical inspection by means of a camera, and can improve an operation efficiency especially in the case of applying a printing to both of two faces of a flexible printed circuit board in comparison with the conventional visual inspection case.

Then, in accordance with an aspect of the present invention, there is provided an inspecting apparatus of a printed state or the like in a flexible printed circuit board comprising:

a working table;

a substrate feeding out unit;

a substrate inverting unit;

a camera inspecting unit;

a substrate inverting unit; and a defect point marking unit for a printed state or the like, wherein the substrate feeding out unit, the substrate inverting unit, the camera inspecting unit, the substrate inverting unit, and the defect point marking unit for a printed state or the like are sequentially placed on the working table along a moving direction of a flexible printed circuit board, the substrate inverting unit inverts the flexible printed circuit board at a suitable timing so as to turn over and feeds out the flexible printed circuit board at a suitable timing in a predetermined direction, the camera inspecting unit moves upward and downward at a suitable timing, and is constituted by a substrate supporting table which oscillates in the substrate moving direction at a desired times in a state of moving upward and drawing the flexible printed circuit board onto the upper surface thereof, and a camera which is held to the upper side of the substrate supporting table by a holing mechanism and moves in a direction orthogonal to the substrate moving direction by a predetermined stroke at a suitable timing, thereby detecting a print defect point in the flexible printed circuit board, the defect point marking unit for a printed state or the like is constituted by a substrate supporting table, and a laser marker which is held to the upper side of the substrate supporting table by a holding mechanism, moves in a direction orthogonal to the substrate moving direction by a predetermined stroke at a suitable timing and oscillates in the substrate moving direction at every time of moving, and a marking is applied to the print defect point in the flexible printed circuit board by the laser marker on the basis of a signal output from the camera inspecting unit.

BRIEF DESCRIPTION OF THE DRAWINGS

FIG. 2 is a plan view of the inspecting apparatus shown in FIG. 1.

DESCRIPTION OF THE PREFERRED EMBODIMENT

Figure 1:
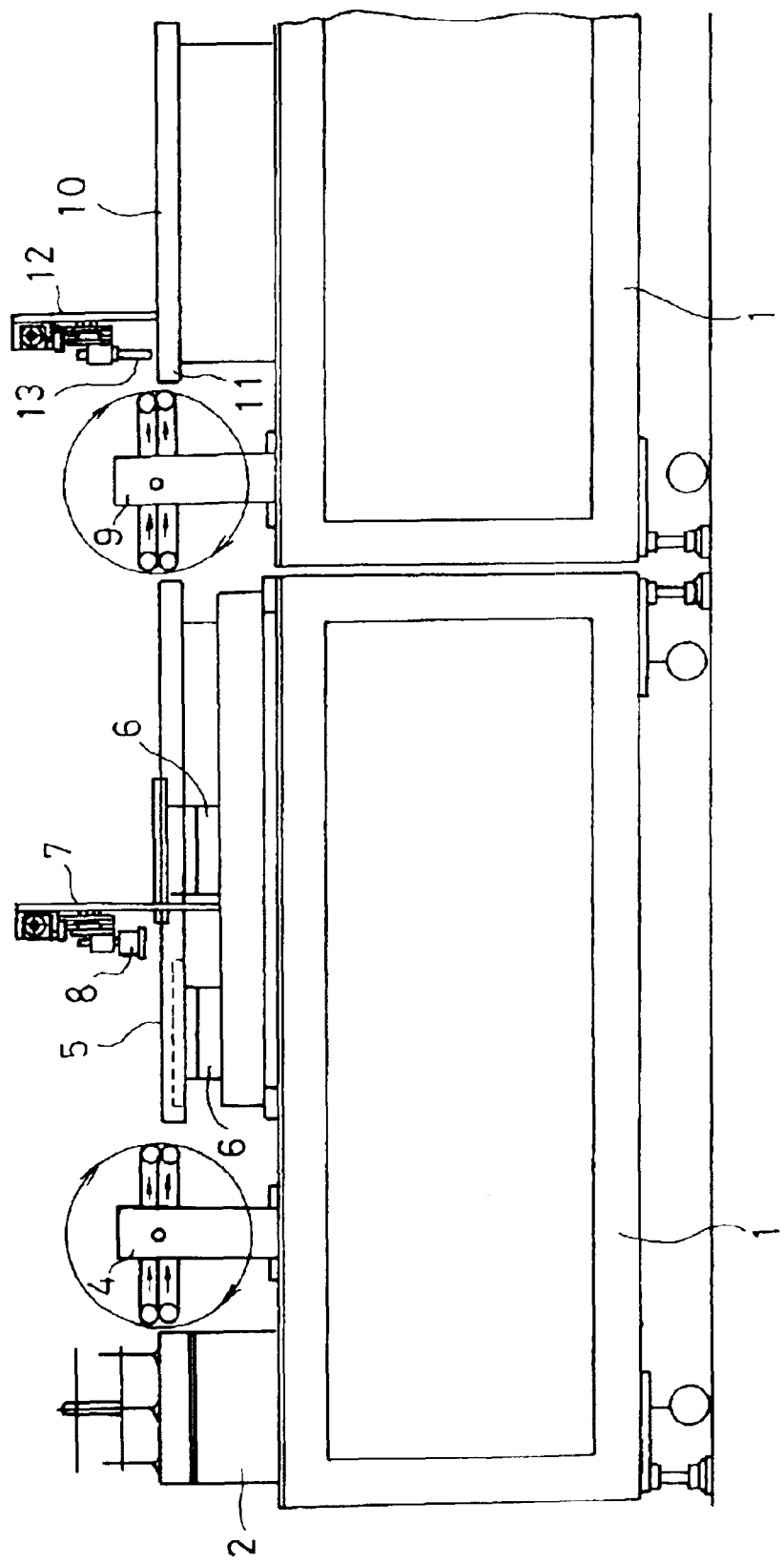
FIG. 1 is a front view of an inspecting apparatus in accordance with an embodiment of the present invention.

A description will be given below of an embodiment in accordance with the present invention with reference to the accompanying drawings.

FIG. 1 is a front view of an inspecting apparatus in accordance with an embodiment of the present invention, and FIG. 2 is a plan view of the same.

In the drawings, reference numerals 1 and 1 denote working tables. Reference numeral 2 denotes a substrate feeding out unit which is placed on the working table 1. Further, the substrate feeding out unit 2 is structured such as to simultaneously feed out two flexible printed circuit boards 3 and 3 in parallel, in the present embodiment.

Reference numeral 4 denotes a substrate inverting unit which is placed at a forward position of the substrate feeding out unit 2 on the working table 1 in a substrate moving direction in such a manner as to be sequential with the substrate feeding out unit 2. The substrate inverting unit 4 is structured such as to turn over the flexible printed circuit boards 3 and 3 at a suitable timing, and to feed out the flexible printed circuit boards 3 and 3 at a suitable timing.

Reference numeral 5 denotes a camera inspecting unit which is placed at a forward position of the substrate inverting unit 4 on the working table 1 in the substrate moving direction in such a manner as to be sequential with the substrate inverting unit 4. Further, the camera inspecting unit 5 moves upward and downward at a suitable timing, and is constituted by a substrate supporting table 6 which oscillates in the substrate moving direction at a desired times in a state of moving upward and drawing the flexible printed circuit board onto the upper surface thereof, and a camera 8 which is held to the upper side of the substrate supporting table 6 by a holing mechanism 7 and moves in a direction orthogonal to the substrate moving direction by a predetermined stroke at a suitable timing.

Reference numeral 9 denotes a substrate inverting unit which is placed at a forward position of the camera inspecting unit 5 on the working table 1 in the substrate moving direction in such a manner as to be sequential with the camera inspecting unit 5. Further, the substrate inverting unit 9 is structured such as to turn over the flexible printed circuit boards 3 and 3 at a suitable timing, in the same manner as that of the substrate inverting unit 4, and to feed out the flexible printed circuit boards 3 and 3 at a suitable timing in a predetermined direction.

Reference numeral 10 denotes a defect point marking unit for a printed state or the like which is placed at a forward position of the substrate inverting unit 9 in the working table 1 in the substrate moving direction in such a manner as to be sequential with the substrate inverting unit 9. Further, the defect point marking unit 10 for a printed state or the like is constituted by a substrate supporting table 11, and a pen-type laser marker 13 which is held to the upper side of the substrate supporting table 11 by a holding mechanism 12, moves in a direction orthogonal to the substrate moving direction by a predetermined stroke at a suitable timing and oscillates in the substrate moving direction at every time of moving.

Next, a description will be given of an operation of the present embodiment. In this case, the present embodiment shows a case in which four flexible printed circuit boards are processed as one set. Two flexible printed circuit boards 3 and 3 which are fed out in parallel from the substrate feeding out unit 2 pass through the substrate inverting unit 4 as they are, and are fed to the camera inspecting unit 5. Accompanying therewith, the substrate supporting table 6 moves upward so as to draw the flexible printed circuit boards 3 and 3 onto the upper surface thereof. Further, in this state, the cameras 8 and 8 are positioned at the upper side in one end side of the respective flexible printed circuit boards 3 and 3 in a length direction and a width direction. Further, at a time when the cameras 8 and 8 are at the positions, the substrate supporting table 6 oscillates one time along the substrate moving direction. Next, the cameras 8 and 8 move by a predetermined stroke in a direction orthogonal to the substrate moving direction, and thereafter, the substrate supporting table 6 again oscillates one time along the substrate moving direction. Next, the camera 8 and 8 again move by a predetermined stroke in the direction orthogonal to the substrate moving direction, and thereafter the substrate supporting table 6 again oscillates one time along the substrate moving direction. These oscillating operations are finished at a time when the cameras 8 and 8 reach end portions of the flexible printed circuit boards 3 and 3 in the opposite side thereto in the width direction.

The flexible printed circuit boards 3 and 3 which are finished in the inspection performed by the cameras 8 and 8 are next fed to the substrate inverting unit 9, are inverted by the substrate inverting unit 9 so as to be turned over, and temporarily stand there.

Next, two new flexible printed circuit boards 3 and 3 are again fed out in parallel from the substrate feeding out unit 2, and pass through the substrate inverting unit as they are so as to be fed to the camera inspecting unit 5, in the same manner as that of the flexible printed circuit boards 3 and 3 which have been inspected by the camera. After the camera inspection is finished by the camera inspecting unit 5, the flexible printed circuit boards 3 and 3 are fed to the substrate inverting unit 4 in the side of the substrate feeding out unit 2, are inverted by the substrate inverting unit 4 so as to be turned over, and temporarily stand there.

Next, the flexible printed circuit boards 3 and 3 which stand in a state of being inverted by the substrate inverting unit 9 in the manner as mentioned above are again fed to the camera inspecting unit 5, and the camera inspection is executed here in accordance with the same operation as mentioned above. Thereafter, the flexible printed circuit boards 3 and 3 pass through the substrate inverting unit 9 as they are, and are fed to the defect point marking unit 10 for the printed state or the like.

Further, at this time, the laser markers 13 and 13 are positioned at the upper side in one end side of the flexible printed circuit boards 3 and 3 in the length direction and the width direction. Then, the laser markers 13 and 13 oscillate one time along the substrate moving direction. Next, the laser markers 13 and 13 move by a predetermined stroke in the direction orthogonal to the substrate moving direction, and again oscillate along the substrate moving direction. Next, the laser markers 13 and 13 again move by a predetermined stroke in the direction orthogonal to the substrate moving direction, and again oscillate one time along the substrate moving direction. Then, at a time of these operations, a marking is applied to the print defect point in the flexible printed circuit boards 3 and 3 by the laser markers 13 and 13 on the basis of a signal output from the camera inspecting unit 5. These repeated operations are finished at a time when the laser markers 13 and 13 reach the end portions of the flexible printed circuit boards 3 and 3 in the opposite side thereto in the width direction. Then, the flexible printed circuit boards 3 and 3 in which the operation is finished are fed out to the next step.

On the other hand, at the same time, the flexible printed circuit boards 3 and 3 which stand in the state of being inverted by the substrate inverting unit 4 are again fed to the camera inspecting unit 5, and the camera inspection is then executed on the basis of the same operation as mentioned above. Thereafter, the flexible printed circuit boards 3 and 3 pass through the substrate inverting unit 9 as they are, and are fed to the defect point marking unit 10 for the printed state or the like. Further, the flexible printed circuit boards 3 and 3 are fed out to the next step after being processed there. In accordance with the operation mentioned above, the process applied to one set comprising four flexible printed circuit boards is completed.

Since the present invention has such structure and operation as mentioned above, in which the mechanical inspection is executed by means of the cameras, the skill which has been required in the conventional visual inspection is not required, and the error by oversight is not generated. Further, especially, in the case that the printing is applied to both of two faces of the printed circuit board, the camera inspection, the inversion, the defect point marking process and the like are executed on the basis of a flow system by means of the machines, and a plurality of flexible printed circuit boards are simultaneously processed. Accordingly, the operation efficiency can be further improved in comparison with the conventional art.

What is claimed is:

1. An inspecting apparatus of a printed state in a flexible printed circuit board, comprising:

a working table;

a substrate feeding-out unit;

a first substrate inverting unit;

a camera inspecting unit;

a second substrate inverting unit; and a print-defect marking unit;

wherein said substrate feeding-out unit, said first substrate inverting unit, said camera inspecting unit, said second substrate inverting unit, and said print-defect marking unit are sequentially placed on said working table along a moving direction of a flexible printed circuit board, wherein said first substrate inverting unit includes means for inverting the flexible printed circuit board and means for feeding out the flexible printed circuit board to said camera inspecting unit;

wherein said camera inspecting unit includes detecting means for detecting the location of a print defect in the flexible printed circuit board, said detecting means including a first substrate supporting table which moves upward and downward with respect to the board moving direction, reciprocates along the board moving direction, and attracts the flexible printed circuit board onto the upper surface thereof when said first substrate supporting table moves upward, and a camera which is held above said first substrate supporting table by a holding mechanism and moves in a direction perpendicular to the board moving direction by a predetermined stroke, wherein said second substrate inverting unit includes means for inverting the flexible printed circuit board and means for feeding out the flexible printed circuit board between said print-defect marking unit and said camera inspecting unit;

wherein said print-defect marking unit includes mark-applying means for applying a marking to the location of a print-defect in the flexible printed circuit board in accordance with a signal from said camera inspecting unit, said marking-applying means including a second substrate supporting table stationary in the board moving direction, and a laser marker which is held above said second substrate supporting table by a holding mechanism, reciprocates along the board moving direction, and moves in a direction perpendicular to the board moving direction by a predetermined stroke, and wherein operations of said first and second substrate inverting units, said first substrate supporting unit, said camera inspecting unit, and said print-defect marking unit are performed at the respective predetermined timings in conjunction with one another.

* * * * *